(12) United States Patent
Turgiss et al.

(10) Patent No.: US 8,027,822 B2
(45) Date of Patent: Sep. 27, 2011

(54) INTERACTIVE, INTERNET SUPPORTED HEALTH AND FITNESS MANAGEMENT SYSTEM

(75) Inventors: Jennifer Lucille Turgiss, Burlington, MA (US); Richard Meer Boylan, Medfield, MA (US); Grant Robert Harrison, Dover, MA (US)

(73) Assignee: Virgin HealthMiles, Inc., Framingham, MA (US)

( * ) Notice: Subject to any disclaimer, the term of this patent is extended or adjusted under 35 U.S.C. 154(b) by 1086 days.

(21) Appl. No.: 11/156,938

(22) Filed: Jun. 20, 2005

(65) Prior Publication Data

US 2006/0287883 A1 Dec. 21, 2006

(51) Int. Cl.
 *G06G 7/58* (2006.01)
 *G01N 33/48* (2006.01)
 *G06F 7/60* (2006.01)
 *G06F 17/00* (2006.01)

(52) U.S. Cl. .................. 703/11; 702/19; 702/20; 703/2; 700/900

(58) Field of Classification Search .................. None
 See application file for complete search history.

(56) References Cited

U.S. PATENT DOCUMENTS

| 6,272,468 | B1 | 8/2001 | Melrose | |
| 6,850,252 | B1 * | 2/2005 | Hoffberg | 715/716 |
| 2003/0229514 | A2 * | 12/2003 | Brown | 705/2 |
| 2004/0120557 | A1 | 6/2004 | Sabol et al. | |
| 2005/0251423 | A1 | 11/2005 | Bellam et al. | |
| 2007/0015974 | A1 * | 1/2007 | Higgins et al. | 600/300 |

OTHER PUBLICATIONS

Rifkin, D.E., "Electronic Medical Records: Saving Trees, Saving Lives," *JAMA* 285(13):1764, Apr. 4, 2001.
International Search Report and Written Opinion with Notification of Transmittal for PCT/US06/23371.
Supplementary European Search issued in European Patent Application No. 06784945.5 dated Dec. 29, 2009.

* cited by examiner

*Primary Examiner* — Shubo Zhou
(74) *Attorney, Agent, or Firm* — Hamilton, Brook, Smith & Reynolds, P.C.

(57) ABSTRACT

A wellness system monitors the controlled progress of patients under surveillance and includes a server base station which is generally off-site, a web-site interface and a local station at the point-of-use, which is generally a health or fitness center. A unique data base is created for each user and goals and objectives may be set with progress monitored. Typically, the user will respond to a survey or questionnaire to populate his specific database. This is combined with a professional assessment and an automated measurement of vital statistics such as weight, blood pressure and body composition as measured at the local station. Other data may be entered manually such as height, age and the like. In a more comprehensive system the invention is designed to monitor other data such as cholesterol and blood glucose, as well. The locally input data may be updated at will by the user or on behalf of the user by professional personnel.

18 Claims, 10 Drawing Sheets fitness assessment   health assessment goal setting

1. got goals?
if you want to win, you need goals. tell us yours.

| Long-term goal | High<br>Next 1-3<br>months | Medium<br>Next 3-6<br>months | Low<br>Next 12<br>months |
|---|---|---|---|
| • lose some weight | O | O | O |
| • gain some weight | O | O | O |
| • fix these nagging health problems | O | O | O |
| • feel better about me | O | O | O |
| • get healthier | O | O | O |
| • get my body back in shape | O | O | |
| • train for these sports (e.g. cycling, rowing, running, sprinting, swimming, racket sports, ball games) | | | |
| • I want to start bodybuilding | | | |
| • other (Please state) | O | O | O |
| • I don't have any goals | O | O | O | goal settings your body talks
are you listening
to it?

(logout)

Fig. 9

INTERACTIVE, INTERNET SUPPORTED HEALTH AND FITNESS MANAGEMENT SYSTEM

BACKGROUND OF THE INVENTION

1. Field of the Invention

The subject invention is generally related to network supported health and fitness systems and is specifically directed to a method and apparatus for interactive IP supported health and fitness systems permitting on-line communication between a user and a central data center.

2. Discussion of the Prior Art

It is known to provide health care data management from a remote location via a networked system. Examples of this technology are demonstrated in a group of patents assigned to Cybernet Systems Corporation.

U.S. Pat. No. 6,723,046 discloses a system for the acquiring medical data from multiple, at-home patient measurement devices and transferring the data via telephone to a remote data management system. The device supports two-way communications between the patient and the database system and is extensible to support multiple plug-in medical devices and devices for patient input or identification. Collection of data is mediated through an interface device that is connected via a digital link to single or multiple patient measurement devices. This interface device is connected to a network via wide area network means including standard phone lines.

U.S. Pat. Nos. 6,375,614 and 6,050,940 disclose a general-purpose system for providing physiological data collection for a variety of medical applications. Programmable input signal acquisition and processing circuits are used so that a plurality of medical signals can be digitized from a common point of contact to a plurality of sensors. A general-purpose data routing and encapsulation architecture supports input tagging and standardized routing through modern packet switch networks. Routing and viewing stations allow for the insertion of automated analysis routines to aid in data encoding, analysis, viewing, and diagnosis.

Other patents generally disclosed networked monitoring systems, see for example, U.S. Pat. No. 5,778,882 which discloses a portable health monitoring system which may be worn by a patient to monitor specific condition, and U.S. Pat. No. 6,148,297 which is directed to a device for monitoring exposure and incident information relating to a health care provider.

U.S. Pat. No. 6,594,607 is directed to a medical screening apparatus for communicating the output of a medical test apparatus to a remote collection site for analysis.

U.S. Pat. Nos. 6,403,897; 6,511,435 and 6,692,436 show a kiosk type of system for a patient for monitoring specific medical conditions. In particular, the '436 patent shows a system designed to be interfaced with a server basically to determine and monitor a reaction to medication regimens.

While useful as medical application and monitoring tools, the prior art systems do not provide a comprehensive interactive system for wellness and fitness wherein the user, health and fitness professionals and the system interface and interact with one another to provide health monitoring and management.

SUMMARY OF THE INVENTION

The subject invention is specifically directed to a wellness program for monitoring and managing the controlled progress of members participating in the program. It comprises four basic components: (1) A data center, generally at an off-site processor, (2) a web-site interface (3) a local station at the point-of-use, which is general a health or fitness center, employee work site, school or other retail areas and (4) personal physical activity devices. An unique data base is created for each user and goals and objectives may be set with progress monitored. Typically, the user will respond to a survey or questionnaire to populate his specific database. This is combined with a professional assessment and an automated measurement of vital statistics such as weight, blood pressure, body fat and BMI as measured at the local station. Other data may be entered manually such as height, age and the like. In a more comprehensive system the invention is designed to monitor other data such as cholesterol and blood glucose, as well. The locally input data may be updated at will by the user or on behalf of the user by professional personnel.

In one embodiment of the invention, the system includes the ability for self-diagnosis on medical devices and testing of the local devices.

In its preferred form, the invention is adapted for protecting the privacy of users by secure means such as, by way of example, a PIN number or other password and secure gateways, including but not limited to fingerprints, retinal scans and the like.

In the preferred embodiment of the invention, the local station is a custom chair-like kiosk with all equipment being housed in a module encompassing the chair. All functions may be completed within the confines of the local station kiosk.

In one embodiment of the invention, incentives are provided to encourage regular use. These incentives may be provided to either or both the health care professional and the user.

In a typical system in accordance with the present invention, the system captures key biometrics, activity level and self assessment. This is collected automatically at the local station and also manually by input for each user generated by a fitness or health professional. Activity tracking is also input on subsequent visits or uses, using automatic measurement devices such as a heart rate monitor, pedometer, accelerometer and the like. PDA's and PC's may also be used to update the user controlled information. In addition, self-assessment information is included such as nutrition and dietary habits, exercise regimen and intervention program assessment.

This information is entered into the database and provides the unique data model for each user. The system then manages and analyzes the data and assigns and tracks each user's progress and maintenance. In one embodiment of the invention, the user is provided with rewards and incentives for (1) maintaining healthful activities (2) meeting certain milestones in assessments and biometrics and (3) improving in assessments and biometrics, and the like. In addition, the individual user input data is analyzed for providing useful feedback information on biometrics, assessments and various healthful activities and for providing a recommended personalized plan for nutrition and exercise. The data is also managed to direct the user to useful information and resources based on the individual needs and lifestyle. Dynamic performance is measured and reminders and course correction recommendations are made.

While the individual user's privacy is not compromised, group data is collected in order to analyze group profiles and health habits. This may be based on age, locale, culture, job category or other information. In addition, special offers and cost savings opportunities may be available to groups such as non-smokers versus smokers, for example.

This analysis of the data is then output from the system to provide individualized reports at the local station, such as biometrics and reward status, assessment results and adherence to a plan or regimen. Personalized action plans are produced and may be modified as results vary. The information may be received at the local station, on PDA's or at the individual's home PC or laptop, and may be reviewed on screen or printed in hard copy form. The collected data is used to drive the customer communications plan. This communication motivates healthy activity and ties it to the incentive awards program wherein the member earns points for redemption of awards.

The body of data is used in group form to provide employers, insurers, retailers and health care systems with group biometrics, group performance and progress toward goals and other useful information.

In all, the system of the present invention provides a comprehensive integrated system and method for maintaining and improving health and wellness in a convenient and automated manner. An individual can progress at any rate he chooses and will be given continuous feedback and recommendations based on his actual rather than perceived adherence to the program. In addition, group data is collected for determining how groups have responded to specific regimens and how group health and wellness is affected by the adherence to or lack of adherence to recommended programs.

BRIEF DESCRIPTION OF THE DRAWINGS

FIG. 9 is a goal setting screen.

DETAILED DESCRIPTION OF THE PREFERRED EMBODIMENTS

Overview of the Invention: The subject invention is ideally a web-based system that offers users a managed, automated system for providing up to date and relevant information as soon as they log in to the site either at a local station kiosk or at other points on the web. By way of example, the user can log in and at any time he can determine:

Accumulated points (for the quarter from January, February, March or April, May, June, or July, August, September or October November December and a total points)
If there is no activity in quarter: (We haven't seen you in the last 30 days text is prompted))
Blood pressure (last recorded blood pressure)
Body Mass Index (last recorded)
Weight (last recorded)
Body Fat (last recorded)
Number of exercise sessions from the logbook (for the quarter as above)
Recognition of improvement prompt and reminders
Recommended reading links to information library.

In addition, a log is kept and displayed, showing the number of times they have logged exercise in the last quarter. Reminders will be generated when regimens are not followed. Recognition will be provided when a users improves on any one of the health measurements. This will provide motivation for the member and also make it more personalized.

In a typical system, data captured at the local station kiosk include:

1. Health Measurements
1.1 Body fat percentage
1.2 Weight
1.3 Blood Pressure
1.4 Daily Heart Rate—measured while blood pressure is being measured.
1.5 Cholesterol
1.6 Glucose
1.7 Height
1.8 Body Mass Index (The combination of height and weight).
2. Fitness Assessment Data
2.1 Fitness Assessment Reports
2.2 Fitness Assessment Questionnaires
3. Health Risk Appraisal (HRA)
3.1 HRA Report
3.2 HRA Questionnaire Health measurements taken at the local station kiosk are uploaded to members' online Personal Folders for personal tracking and monitoring. The navigation is simple and flexible. This functionality allows members to view any chosen measurement over any time period they choose. i.e. last six month, last 6 weeks, last 5 days, (from a date in and date out option) and compares it against the ideal ranges for each measurement.

Figure 1:
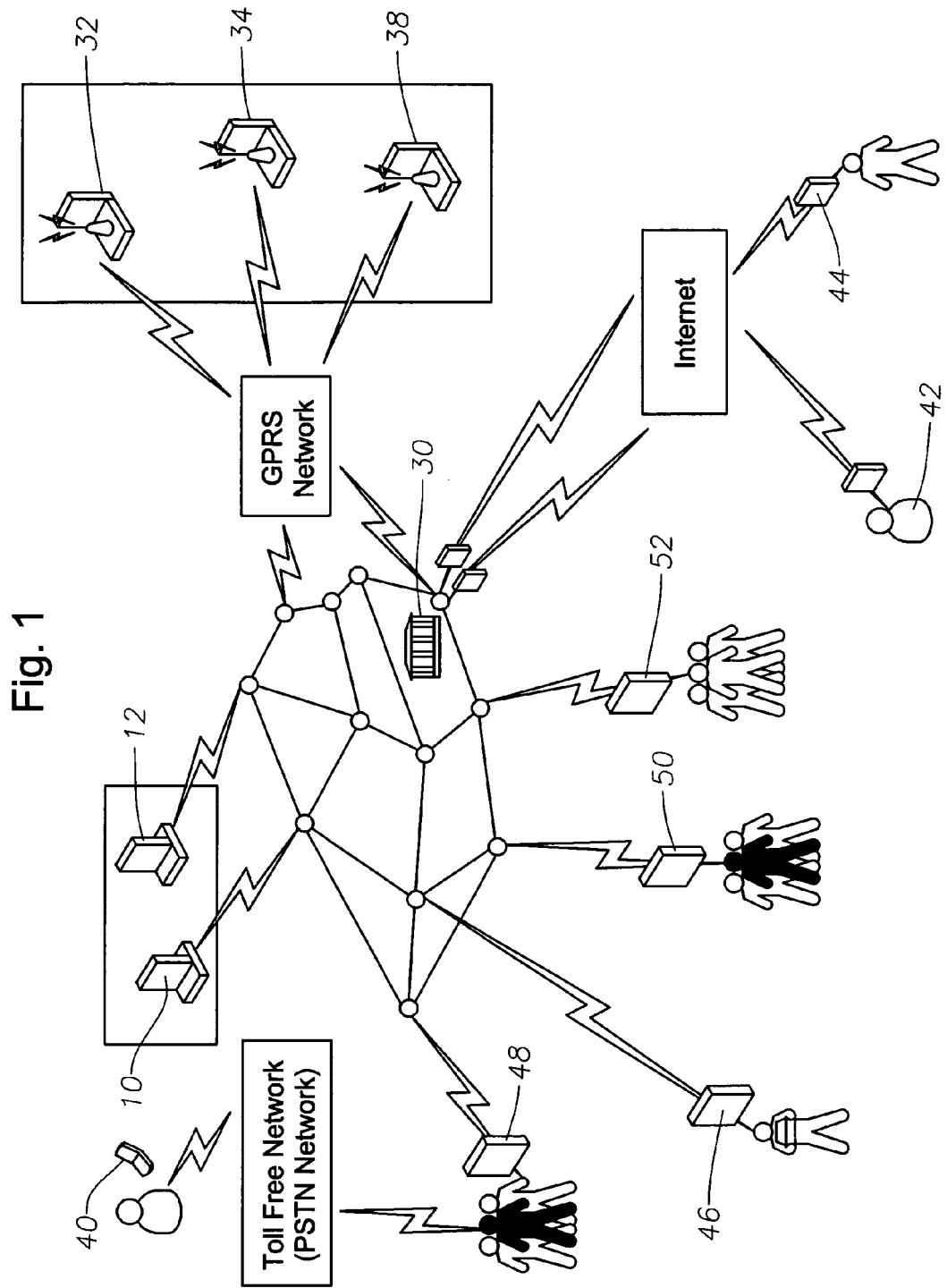
FIG. 1 is an overview of the network system in accordance with the present invention.
Figure 2:
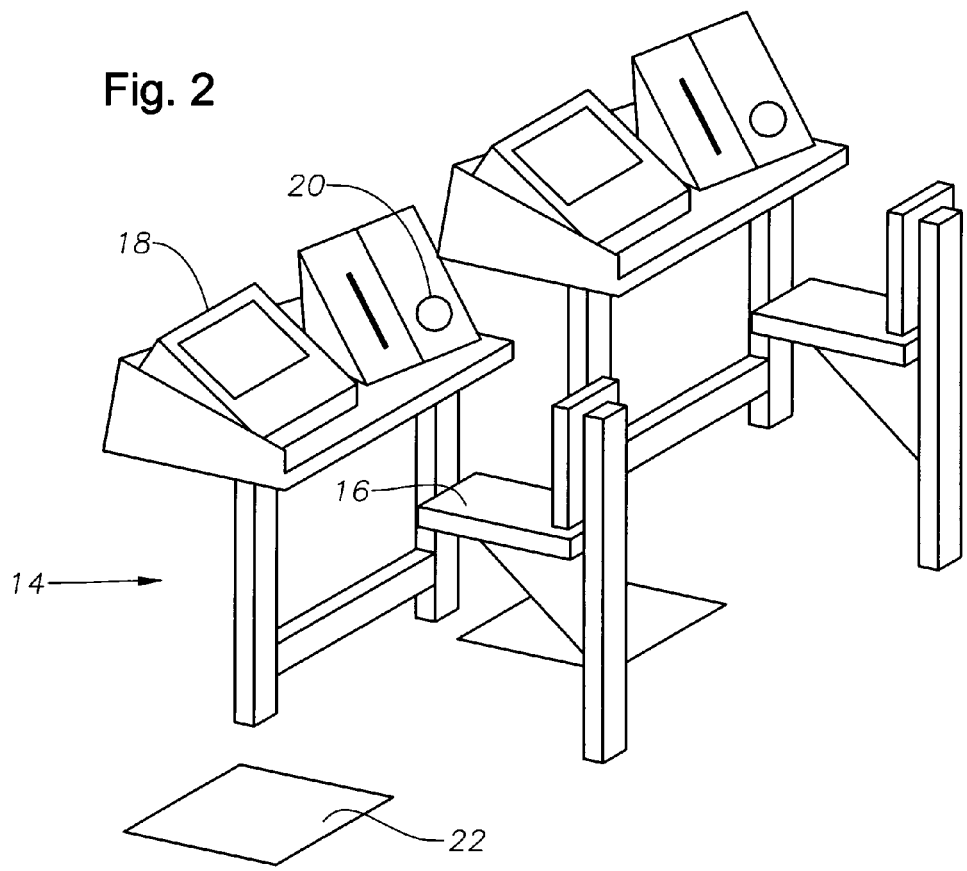
FIG. 2 is a data kiosk for a local station.
Figure 3:
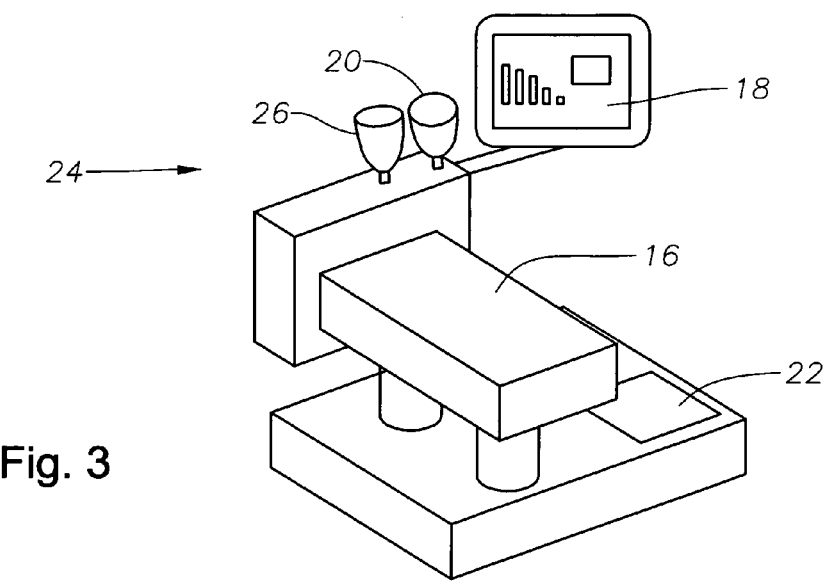
FIG. 3 is an alternative data kiosk for a local system.

The data is displayed in a variety of formats, making the information easy to understand. These include:
Graphs/Bar Charts
Written Reports
Comparison Windows showing Progress
Tables and Schedules Description of the Drawings: FIG. 1 is a system configuration diagram. The heart of the system is the local station kiosk as shown at kiosks 10 and 12. One or more of these kiosks are physically located at a health or fitness facility, or other public or semi-public location such as, by way of example, country clubs, health clubs, universities, schools and the like. Two kiosk configurations are shown in FIGS. 2 and 3, respectively. The kiosk 14, shown in FIG. 2 includes a chair 16, a touch screen 18, a blood pressure monitor 20 and a scale 22. The touch screen is used to input manual information such as height, age and the like. The touch screen also provides the feedback to the kiosk in a display readable by the user. The kiosk 24 of FIG. 3 is similar to the kiosk 14 in that it also includes a bench or chair, a touch screen 18, a blood pressure monitor 20 and a scale 22. However, the kiosk 22 also supports connectivity to other monitoring and measurement devices as indicated at 26.

Returning to FIG. 1, the data for a user is collected at the local station kiosk and transmitted over a network to a central server 30, where the data is archived as a unique data base for each user. The date then may be accessed at any kiosk in the system, as indicated at kiosks 10, 12, 32, 34 and 38. The user may also access the data using a PDA or cell phone 40, a PC 42, or other monitor device 44. Registered health care partners may also access the data via the network as indicated at 46. Group information useful to the insurance industry, employers and possibly retailers is made available over the network as indicated at 48, 50 and 52.

A plurality of typical touch screens are shown in FIGS. 4-9.

Figure 4:
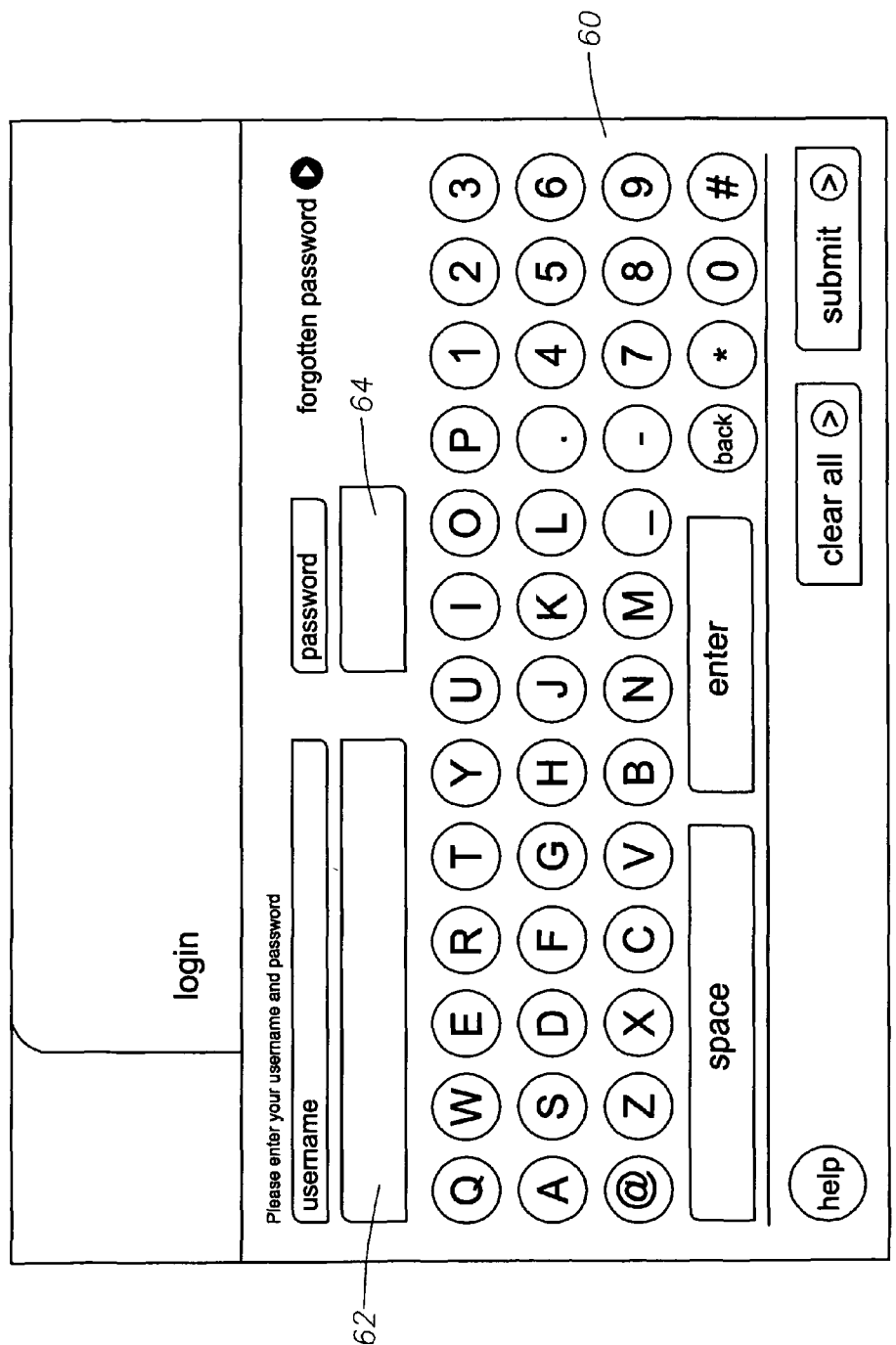
FIG. 4 is an illustration of a typical data entry module for a local data kiosk.

The touch screen of FIG. 4 is the log in screen. This screen includes a typical alphanumeric keyboard 60 and screens for the user name 62 and user's password 64. Manually input data is entered on this or a similar screen with the alphanumeric keyboard.

Figure 5:
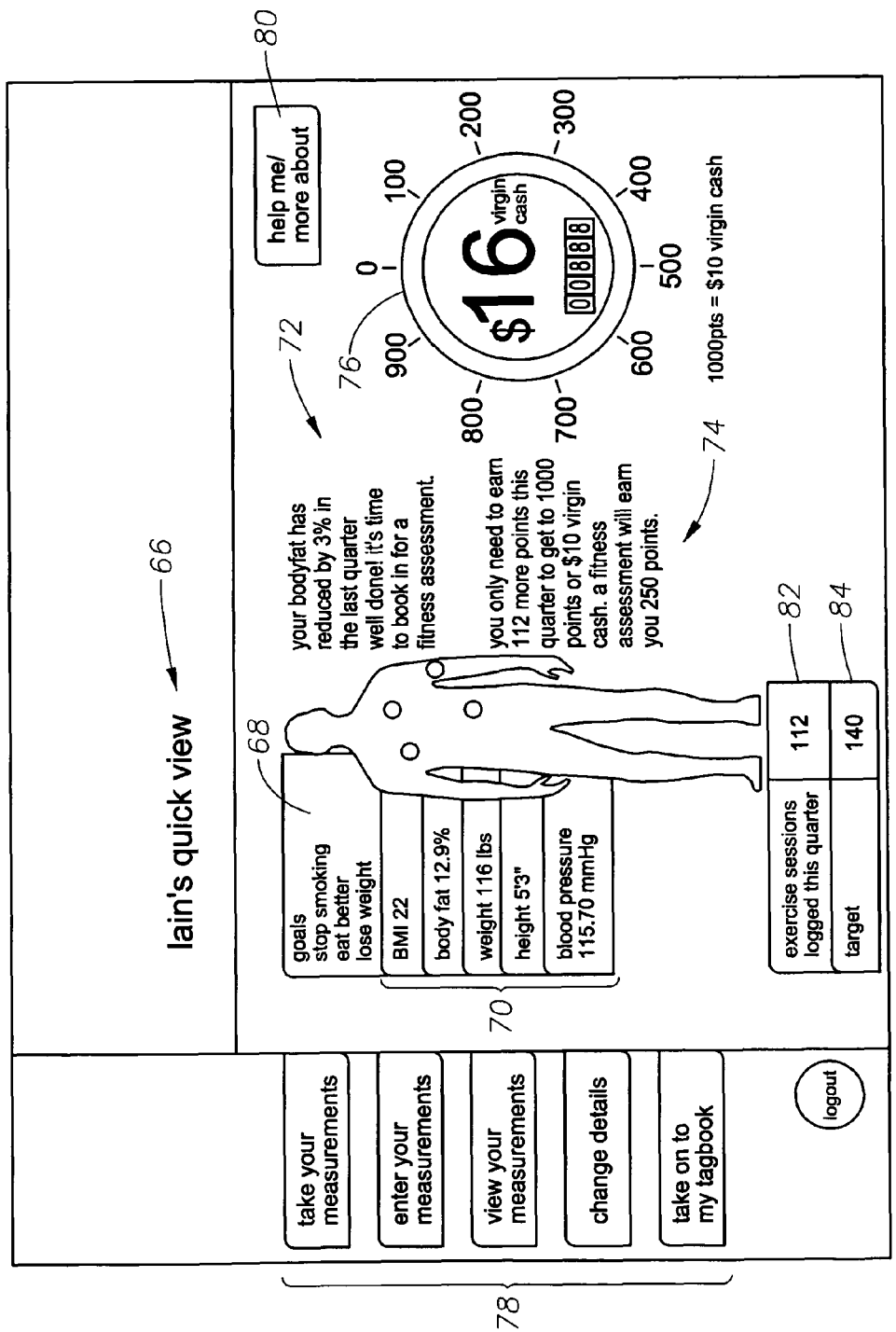
FIG. 5 is a typical overview screen showing the data for a specific individual.

The touch screen of FIG. 5 is a typical "quick view" giving a one screen assessment and readout display of current data in the data base for the user. The user is identified as indicated at 66. Specific user goals are displayed at 68 as well as specific biometric information as indicated at 70. Performance statistics are displayed at 72 and reward progress at 74, 76. Touch windows 78 and 80 will permit the user access to other screens. Personal goals and progress are displayed at 82, 84.

Figure 6:
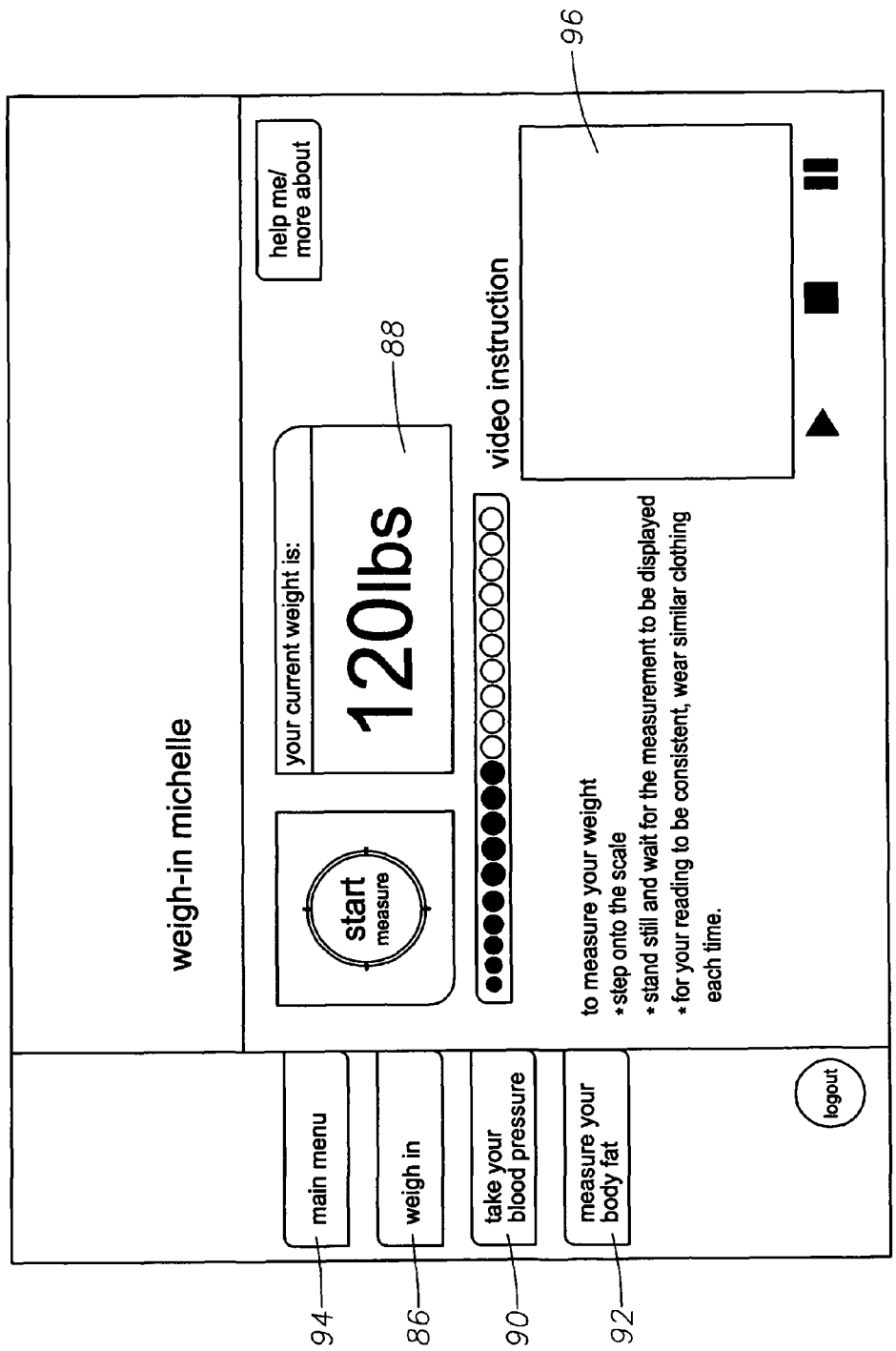
FIG. 6 is a typical screen showing automated data entry.

The touch screen of FIG. 6 shows an example of an interactive screen which is accessed from the screen of FIG. 5. In this example, the user would press the "take your measurements" window of screen 5 to access the screen of FIG. 6. This will permit the user to then weigh in when he presses the "weigh in" window 86 of the screen of FIG. 6. When he steps on the scale 22 of the kiosk 14 or 24 (FIG. 2 and FIG. 3, respectively) his current weight automatically will be displayed at window 88 of the screen of FIG. 6 and collected in the data base. He can touch other windows such as the blood pressure window 90 or the body fat window 92 to access other screens. He can also return to the main menu as indicated at window 94. Video instructions for completing the task, in this case entering weight, can be displayed at window 96.

Figure 7:
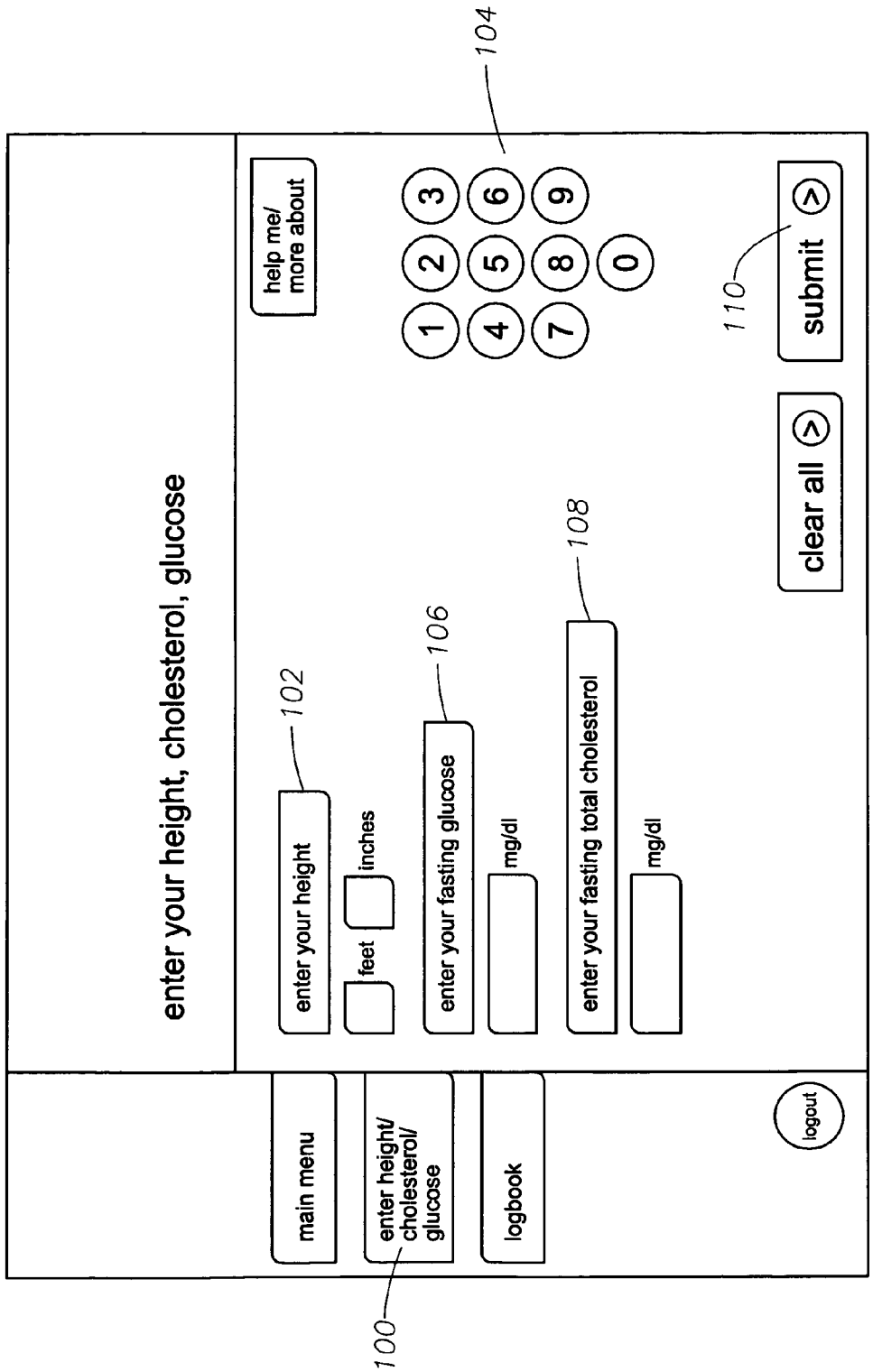
FIG. 7 is a typical screen showing manually input data.

The touch screen of FIG. 7 illustrates a screen where the data is manually input by the user or by a fitness professional, as opposed to the automatic entry of the screen of FIG. 6. In this case, the user has touched the "enter height/cholesterol/glucose" window 100. He will then touch the "enter your height" window 102 and the touch number pad 104 to enter his height. He like wise enters his glucose by touching window 106 and his total cholesterol by touching window. Once the task is completed, he submits the information by touching the submit window 110.

FIGS. 6 and 7 are but two examples of the data entry screens available to the user, and are used as examples herein to demonstrate automatic data collection (FIG. 6) and manual data entry (FIG. 7).

Figure 8A:
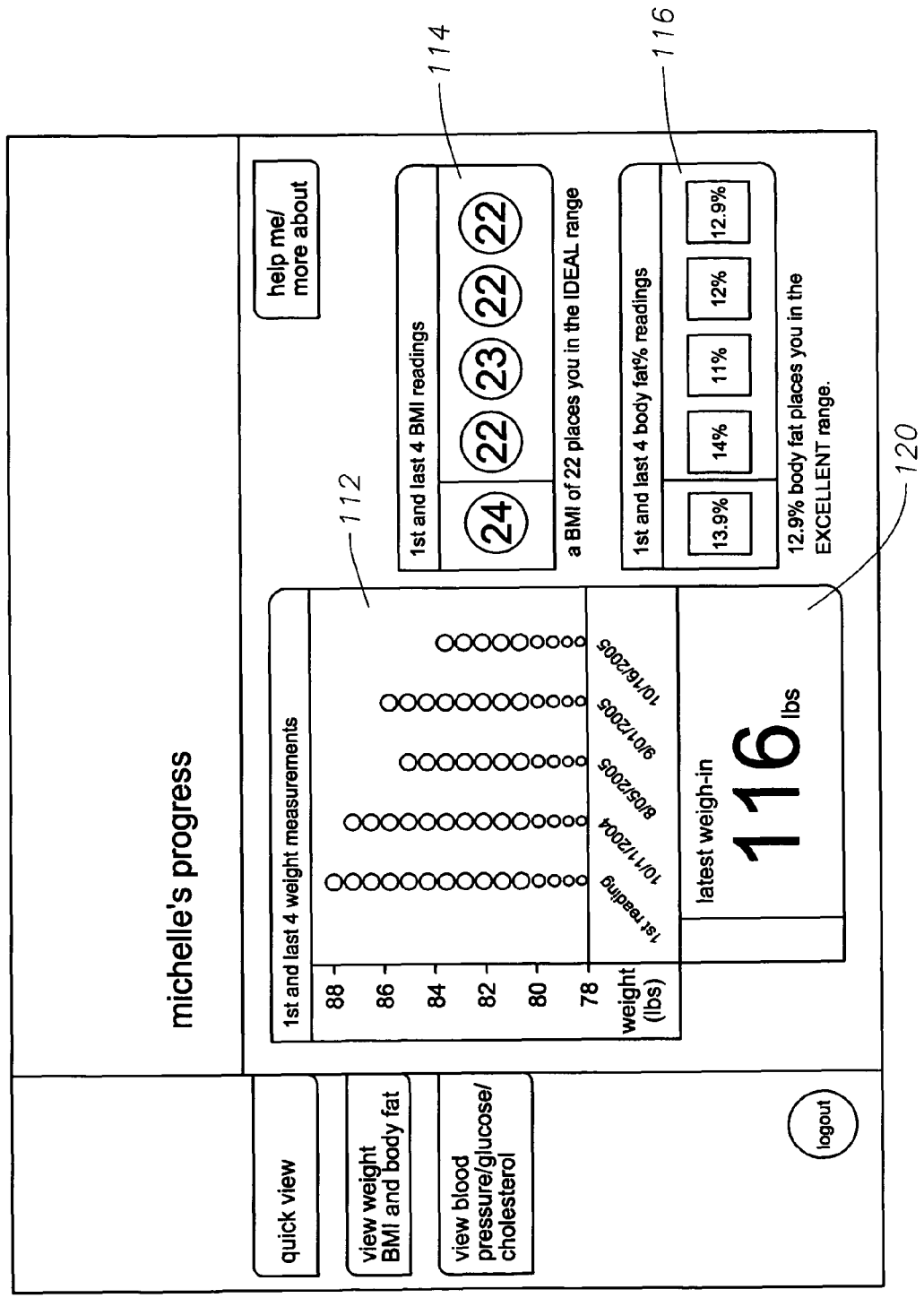
FIGS. 8a and 8b are a progress report screens.
Figure 8B:
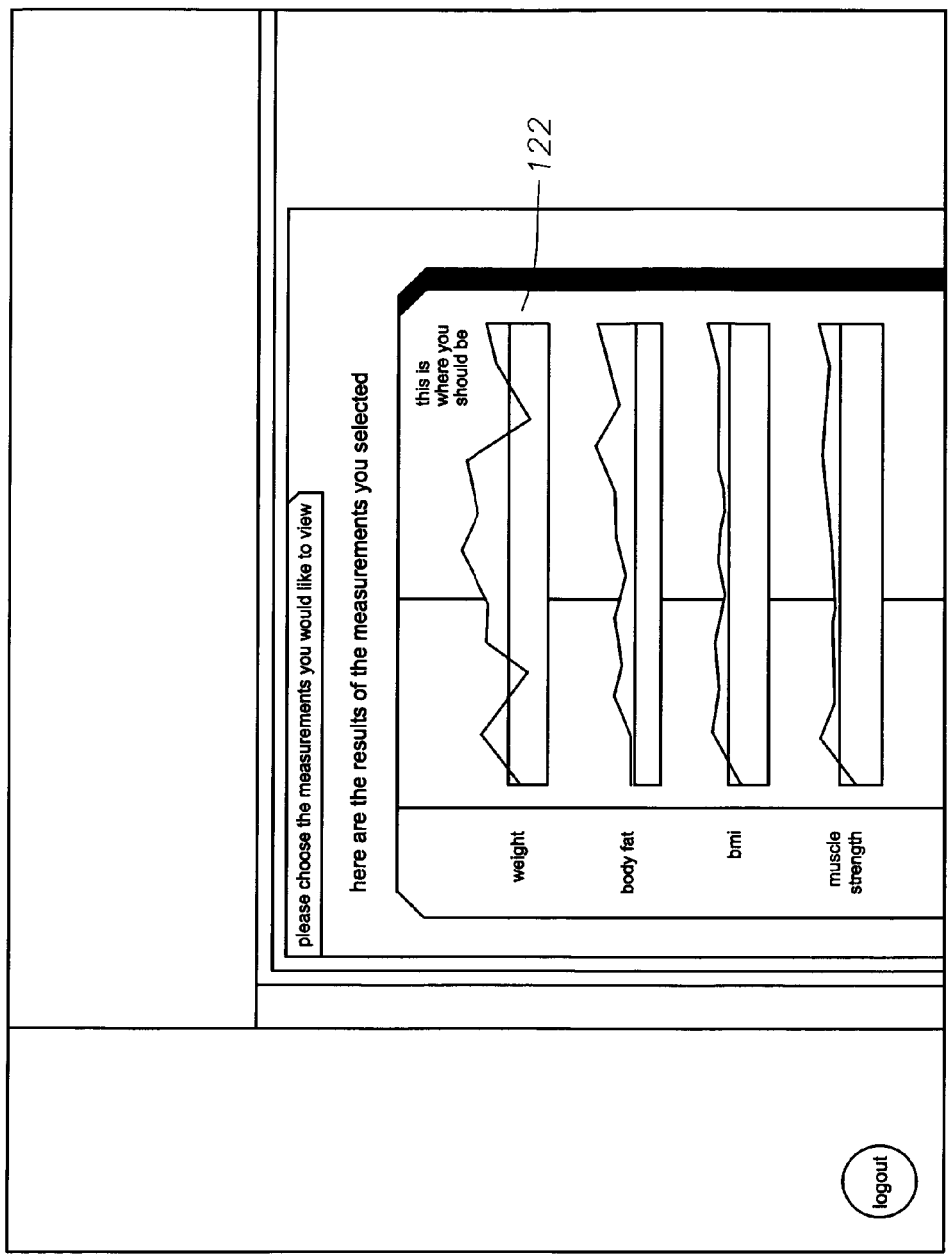

FIGS. 8a and 8b are examples of assessment screens wherein the user is provided with graphic information showing his progress. In the screen of FIG. 8a it can be seen the history of weight measurements is shown in window 112 in bar graph form. A numerical display of BMI is shown in window 114 and body fat is shown in window 116. Previous weight at last weigh-in is shown in window 120. As shown in the screen of FIG. 8b, the user can select certain biometric information to track and it can be shown in line graph format as shown in the window 122.

FIG. 9 shows an input screen where the user can set individual goals, as indicated.

While touch screens are shown, it should be understood that the information can also be accessed using a standard screen and a mouse to point a click on the various windows, particularly when remote access screens are accessed by the user via a home PC or a laptop, for example.

The heart of this system is the software and a description of an exemplary system thereof follows.

The measurements taken at the local station kiosk are:
1.1 Body fat percentage
1.2 Weight
1.3 Blood pressure The kiosk allows the entry of the following measurements:
1.4 Glucose
1.5 Cholesterol
1.6 Height The combination of height and weight gives feedback on BMI (Body mass index).

These measurements can be viewed and tracked at the kiosk touch screen.

In addition to taking and entering these measurements at the kiosk, a member has access to the following functionalities:
1.7 Exercise logbook
1.8 Update contact details
2. Evaluation of Kiosk Measurements
2.1 Body fat percentage. A single value is presented at the kiosk touch screen. In the alternative this is shown in comparison with the normal range of values with an evaluation of poor to excellent.
2.2 BMI. The measurement, norms and an interpretation of the value should are displayed straight after measurement as in body fat.
2.3 Blood pressure (mmHg). The measurement, norms and an interpretation of the value should be displayed straight after measurement, e.g.: Your blood pressure of 140/90 mmHg is higher than the normal recommended value, please redo the measurement after 2 to 5 minutes of rest.
2.4 Glucose. The measurement, norms and an interpretation of the value should be displayed straight after measurement, e.g.: You should aim to reduce your current glucose value of xxxxx, to the recommended level.
2.5 Cholesterol. The measurement, norms and an interpretation of the value are displayed with the actual measurement, with recommendations, e.g.: You should work to reduce your current cholesterol value of xxxx to the recommended level.
2.5 Daily HR (bpm). While measuring blood pressure, the pulse rate is also measured and displayed. Members are encouraged to evaluate their resting pulse in relation to training status, time of day and circumstances of measurement.
3. Additional Features on the Touch Screen:
3.1. Logbook. The logbook facility on the kiosk is the same version as the website. The member can obtain and log-in the same information at both places.
3.2 Screensaver. The kiosk system includes a screen saver that is active when the kiosk touch screen is not in use.
3.3 Update Cell Phone Number and Email Address. Members are able to update their contact details at the Touch Screen, and also indicate their preferred contact method.
3.4 Contact Us for more information. Members may receive more information/interaction with the kiosk sponsors if they are unsure of their measurements. If they select the "Contact Us" button on the touch screen, they will be prompted to edit and verify the contact details we have for them in our system. They will also be asked to indicate their preferred contact method. The sponsor will then contact them and discuss their concerns around their health measurements.
3.5 Health Flags. Members with high blood pressure, cholesterol and glucose will be flagged in the sponsor system for contact.
4. Help Text on the Touch Screen. The purpose of the Help Me! section is to assist members to easily find the information they need regarding their measurements. A link to this information is available from the main page of each measurement. The Help Me! section for each measurement is broken down into 5 simple questions:
1. How to do your measurement correctly.
2. What your values mean.

3. What the technology behind the measurement is.
4. How the technology has been scientifically validated.
5. Troubleshooting guide to your measurement.
4.1. Help Me with Body Fat
How to do Your Body Fat Measurement Correctly.

Ensure that the lid is firmly closed before you insert your card.

Once instructed, lift the lid and place your triceps (back of your upper arm) horizontally on the lever arm.

Slide the cap down so that it rests firmly on your bicep (front of your upper arm).

Once you have secured the cap, push the black button.

Remain in this position until the measurement is displayed on the screen.

Lift cap, remove your arm and close firmly.

What Your Body Fat Values Mean.

Body fat percentage refers to the percentage of your body weight that is fat tissue and is largely determined by your genetic make-up and lifestyle behaviour. Excess body fat can be associated with many chronic diseases.

What the Technology Behind the Body Fat Measurement is.

The preferred embodiment of the system measures body fat a near-infrared device which is based on the measurement from the near-infrared (NIR) reader. This reader is based on the principle of light absorption and reflection. Body fat absorbs the near infrared light and lean body mass (muscle) reflects the light.

How the Body Fat Measurement Technology has been Scientifically Validated.

FULL ARTICLES ARE AVAILABLE ON THE USER'S PERSONAL FOLDER. Studies performed by the Exercise Science and Sports Medicine Faculty of University of Cape Town, South Africa have shown that both skinfold measurements, measured by a skilled anthropometrist, DEXA, and near-infrared reactance as measured by the system, are very closely correlated. Importantly, these studies suggest that at lower levels of body fatness, skinfolds may actually underestimate body fat % and at higher levels, they may actually over-estimate body fat %. In these cases, system readings may be more accurate and consistent over time.

Troubleshooting Guide to Your Body Fat Measurement.

If you experience irregular body fat readings:
Ensure you calibrate the device with the lid closed, and not on your arm.
Ensure there has not been a major weight fluctuation.
Ensure that you are measuring on the same level of the bicep each time.
Always use your right arm.
Take your measurements at similar times of the day.
Error Reading:
Ensure the lid is closed.
Keep the lid closed until it tells one to lift it.
Ensure that the lid lies flat over the bicep for the duration of the measurement.

4.2. Help Me with Blood Pressure
How to Measure Blood Pressure Correctly
Sit down, relax.
Roll up the sleeve of your right arm, so that your upper arm is bare.
Ensure that there is no restriction or tight clothing around the upper arm.
Place your arm, palm up, all the way through the cuff
Your elbow rests in the groove of the arm support. The cuff should be positioned around your upper arm.
Press the black button to begin the measurement.
Remain seated, keep your arm still and relaxed and remain quiet until the measurement has been completed.

What Your Blood Pressure Measurement (Systolic and Diastolic Values) Mean

Blood Pressure is the pressure of blood against the walls of the arteries of the cardiovascular system. When the heart forcefully contracts the pressure is increased (systolic pressure—top value) and as the heart relaxes the pressure decreases (diastolic pressure—bottom value). The risk of cardiovascular disease is increased with high blood pressure (hypertension).

Classification of Blood Pressure

| Classification | Systolic (mmHg) | Diastolic (mmHg) | |
| --- | --- | --- | --- |
| Desirable | <120 | <80 | Excellent |
| Prehypertenstion | 120-139 | 80-89 | Good |
| Stage 1 | 140-159 | 90-99 | |
| Stage 2 | >160 | >100 | |

Low blood pressure or Hypotension is not usually a sign of underlying disease. A persistently low blood pressure requires assessment of lifestyle (smoking, poor nutrition, lack of exercise) and medical opinion may be necessary.

What is the Technology Behind Blood Pressure Measurement

The preferred embodiment of the system uses a UEDA or Omron device which measures blood pressure based on sound and pressure.

How has the Blood Pressure Device has Been Scientifically Validated

FULL ARTICLES ARE AVAILABLE ON EACH MEMBER'S PERSONAL FOLDER

Troubleshooting Guide to Blood Pressure Measurement
If you cannot get a reading, make sure:
Your arm is fully inside the unit, with the elbow in the elbow groove
Your palm is facing upwards
You do not move during the measurement
You do not talk during the measurement
You keep your arm inside the unit until the measurement is finished.
If your Blood Pressure reading is excessively high, rule out these factors related to measurement technique first:
Did you talk during the test? (the microphone in the blood pressure unit is very sensitive)
Was there was a lot of noise around you as you took this measurement?
Did you move during the test?
Did you remove your arm before the measurement was finished?
Have you had any stressful event that could have affected this reading?
Did you have caffeine related products that could increase your blood pressure?
If none of these apply, and your readings are excessively high, we recommend that you consult your doctor to be safe.
If your Blood Pressure reading is excessively low, remember that your blood pressure will drop after exercise. To check your measurement, repeat it and make sure that:
Your right arm is placed correctly inside the unit, with the cuff around the upper arm
Your right palm faces upwards
You do not talk during the measurement
You minimise the noise around you as you take the measurement
If your readings are very low, you should consult your doctor.

4.3. Help Me with Weight and Body Mass Index

How to Do Your Weight Measurement Correctly.
- Step onto the scale.
- Stand still and wait for the measurement to be displayed.
- For consistent readings, please ensure you wear similar clothing each time you weigh yourself.

What Your Weight and Body Mass Index Values Mean.

Body Mass Index (BMI) is a ratio of your weight to your height (wt/ht$^2$). Body composition and in particular, body fat measurements are becoming an increasingly important component of health risk appraisal. Please note: Your BMI measurement is primarily an indicator of your risk for developing chronic disease. It is not a good predictor of your ideal weight. For example, rugby players may have a high BMI but are physically active and fit.

What the Technology Behind the Weight Measurement is.

The system uses an Adam-Lab or Omron scale that has 4 load cells that distribute weight evenly.

How this Weighing Technology Been Scientifically Validated.

FULL ARTICLES ARE AVAILABLE ON EACH MEMBER'S YOUR PERSONAL FOLDER

Troubleshooting Guide to Your Weight Measurement.
- Ensure that you always wear similar amounts of clothing
- Always take your measurement either with or without your shoes on—consistency is key!
- Stand still with your weight evenly distributed over both feet while taking your measurement
- Avoid taking your weight measurement directly after a large meal or consuming large amounts of fluids
- Also, be aware that fluid loss (e.g. through sweat loss) may impact on your measurement

4.4. Help Me with Cholesterol

How to do Your Cholesterol Measurement Correctly.

Cholesterol can either be determined by a finger-prick test or a full blood test. A finger-prick test is a simple procedure that can be performed by a health professional, and involves a relatively pain-free finger-prick that produces a drop of blood from which the analysis is done. Please note that this is a screening assessment and is not as accurate as a full blood test.

A fasting blood test will provide information about the different types of cholesterol (total cholesterol, HDL, LDL and triglycerides). It is important to understand what type of cholesterol is being tested and to ensure that the interpretations of the results are accurate. All elevated test results should be verified by a doctor.

What does Your Cholesterol Value Mean.

Cholesterol is a fat-like substance (lipid) that not only circulates in the blood, but also plays an important role in the formation of cell membranes and certain hormones. Cholesterol causes problems when it sticks to the inner walls of the blood vessels and results in narrowing of these vessels. This obstruction and decreased blood flow to the heart may result in raised blood pressure; or to angina or a heart attack if the flow is totally obstructed. Interrupted blood flow to the brain can lead to a stroke.

There are various causes of a high total cholesterol level. These include: a family history of elevated cholesterol, a diet high in saturated fats and low levels of physical activity.

4.5. Help Me with Glucose

How to do Your Glucose Measurement Correctly.

Testing blood glucose in a systematic way is the cornerstone of good diabetes care. You can either perform a self-measurement, or your doctor may ask you to take a Fasting Plasma Glucose (FPG) test to determine whether you have high blood sugar. Before the test you'll be asked to avoid strenuous exercise and not drink or eat for at least 12 hours before the test. The FPG is a reliable test that requires one blood sample.

What does Your Glucose Value Mean.

Glucose is the simple sugar that your body obtains from the foods you eat When you have insufficient insulin, or when your body is unable to use the insulin you manufacture, an excess of glucose builds up in your blood, and you have elevated blood glucose (or blood sugar) levels.

4.6. Help Me with Height

How to do Your Height Measurement Correctly.

Your height is taken from the floor or measuring platform to the highest point of the skull. You must stand barefoot with your arms hanging by your sides. Your heels, buttocks, upper back and head should be in contact with the wall or measuring equipment. Look straight ahead, stand tall and take a deep breath. Your measurement should be recorded to the nearest inch.

What does Your Height Value Mean.

Your height measurement is a measurement of your stature. It is used in calculations for Body Mass Index (BMI) as well as estimations of Body Fat percentage.

4.7. Help Me with Daily Heart Rate

How to do Your Daily Heart Rate Measurement Correctly.

Your daily heart rate is calculated at the same time as when you take your blood pressure reading at the kiosk. In order to measure it correctly follow the instructions below:
- Sit down at the blood pressure device, relax.
- Roll up the sleeve of your right arm, so that your upper arm is bare. Make sure that any clothing is not restricting your blood flow,
- Place your arm, palm up, all the way through the cuff.
- Your elbow rests in the groove of the arm support. The cuff should be positioned around your upper arm.
- Press the button to begin the measurement.
- Remain seated, keep your arm still and relaxed and remain quiet until the measurement has been completed.

What Your Daily Heart Rate Value Means.

Daily resting heart rate is the number of heart beats in one minute when you are at rest.

The system measurement is an indication of your average daily heart rate, and may be affected by factors such as your mood state, stress levels, caffeine and surrounding noise in the environment you took your measurement.

The most accurate way of measuring your resting heart rate is in the morning, after a good night's sleep, and before you get out of bed.

Resting heart rate usually rises with age, and is generally lower in people who are physically fit.

Resting heart rate is used to determine one's training target heart rate. Athletes can monitor their resting heart rate as one way to find out if they're over-trained.

What the Technology Behind the Daily Heart Rate Measurement is.

The system's automatic UEDA or Omron blood pressure device picks up heart sounds as well as pressure through the use of a microphone and therefore can also produce a daily heart rate measurement.

How the Daily Heart Rate Technology has Been Scientifically Validated.

In order to effectively monitor and track daily heart rate, it is essential to use a consistent measuring technique. In other words, to monitor daily heart rate over an extended period of time, it is important not to use and compare different techniques. In a similar way, it is important to always weigh yourself on the same scale, as not all scales are calibrated the same and so will read consistently differently.

Troubleshooting Guide to Your Daily Heart Rate.
  If you cannot get a reading, make sure:
    Your arm is fully inside the unit, with the elbow in the elbow groove
    Your palm is facing upwards
    You do not move during the measurement
    You do not talk during the measurement
    You keep your arm inside the unit before the measurement is finished.
  If your reading is very high:
    Daily heart rate fluctuates all the time depending on the situation and even time of day. For example if you measure your daily heart rate in the morning and then in the evening the readings will most probably be slightly different. Caffeine (coffee or coca cola) will also affect your readings as well as stress, fatigue, your body temperature and even talking whilst you take your measurement. Also do not forget that resting heart rate increases with age.

The Log Book:
Strategic Objective:
1. The logging on the system is the same as the system (quick log).
2. The system will also have the choice of a more comprehensive logging/tracking system for those members who like to track more detail in their workouts.

Step One—Enter the Date of Your Session
  Text Prompt: Please enter the date of your exercise session
  Very simple calendar, displaying days of the month, with an option to scroll to other months Step Two—Enter Activity Type
  Text Prompt: Please enter the type of activity you performed during this session:
  Members then have a choice of choosing activities from:
  Cardiovascular
  Group exercise class
  Recreational exercise
  Strength exercise
  Stretching
  Played sports Step Three—Enter the Duration of Activity
  Text Prompt: Please enter the duration
  Members then have options to select the duration in:
hours (1-24)
minutes (1-59)

Step Four—Enter the Intensity of Activity
  Text Prompt: Please enter the intensity or effort level of each activity selected
  Rate of Perceived Exertion (RPE) scale should appear with the following options for member to select:
    0 Rest
    1 Very easy
    2 Easy
    3 Moderate
    4 Somewhat Hard
    5 Hard
    6 Harder than hard
    7 Very Hard
    8 Very very hard
    9 Maximal Step Five—Save Your Sessions
  As each session is completed, members must be prompted to save it before they exit the application
  There must also be an option to delete a session
  Display the accumulated totals:
1) Time for that session entered
2) Calories burned for that session
3) Time accumulated for the month
4) Calories accumulated for the month
  Calculation of total time:
  Per session
    Details logged by member
  Per week
    Add each session's total time logged for the week in question
    Display in hours:minutes
  Calculation of Calories:

$$Kcal/\text{minute} = \{(\text{Intensity (Average } METs) \times 3.5 \times \text{body weight in kg})/200\} \times \text{duration in minutes}.$$

Figure 10:
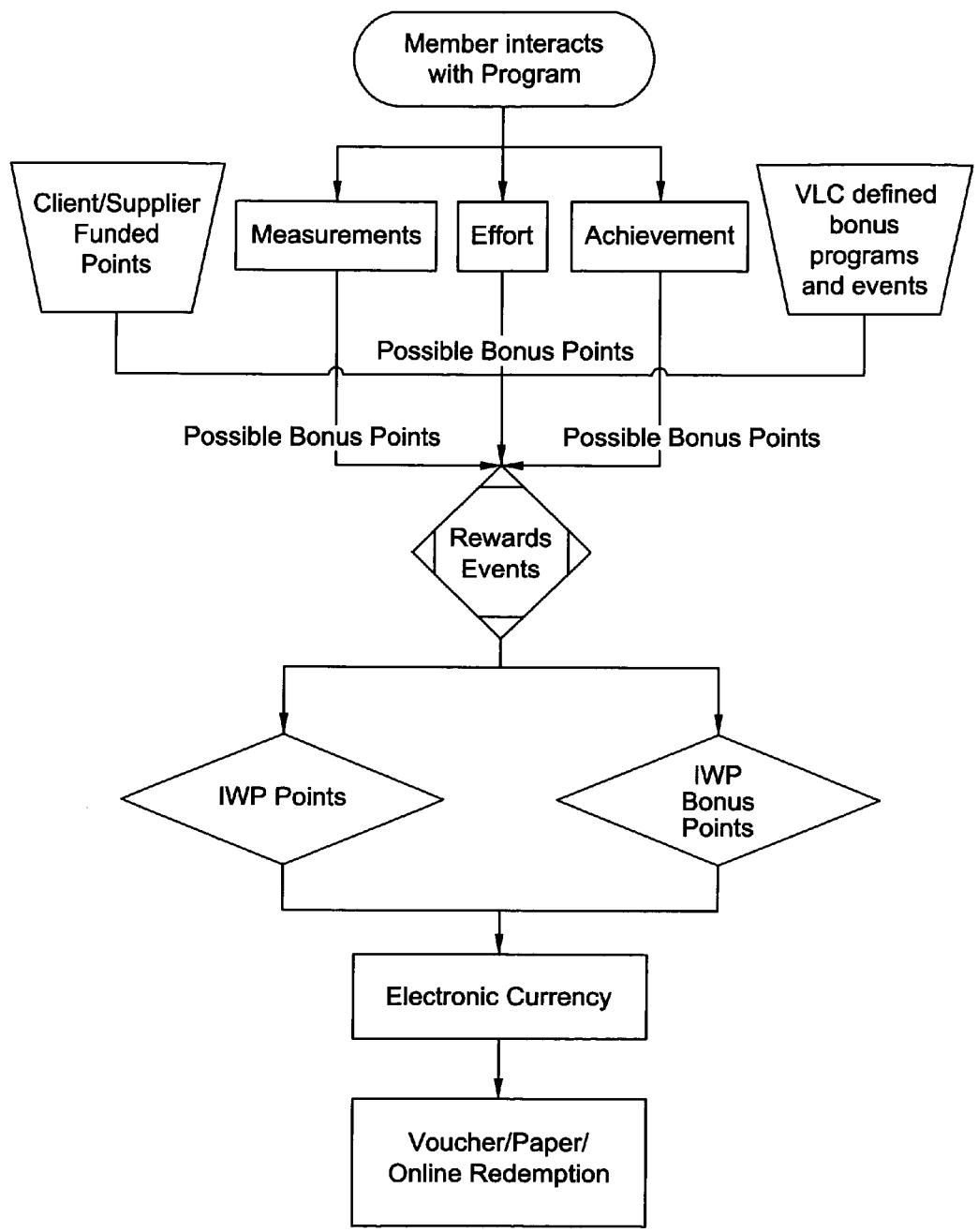
FIG. 10 is a flow chart of the rewards program.

Rewards Program
  The rewards program or the Wellness Program (IWP) is an important optional feature of the system in accordance with the teachings of the subject invention. A flow diagram for the rewards program is illustrated in FIG. 10. The basic 'currency' of the IWP will be points accumulated by members, which they will be able to convert to useable currency and then redeem against a wide variety of rewards. Like any currency, points will be intrinsically valuable and members will need to be able to understand easily the relative earning potential of a wide range of activities and contact events that will constitute their interaction with the IWP.
  The core objective of the IWP is the ability to reward people for effort and activities which go towards improving their own fitness and wellbeing.
  Points are earned through:
  Measurement
  Effort
  Achievement
  Bonus points can also be earned by members through other methods that are selectively defined by the operator.
  There are three classifications of point's allocation:
  1. The Standard Program—this is defined as those aspects that are incorporated in the monthly 'rewards membership' fee. They are parts of the program that all rewards members have access to AND they are key drivers of health behaviour change. These include:
    IWP Registration and Health Snapshot completion
    Health Zone measurements
    Fitness Assessments
    Self logged exercise
    Electronically logged/uploaded exercise
    Quest
  2. The Client/Supplier Funded Program—this is defined as those points that a employer may request asking to double the Health Snapshot points allocation where the employer would be charged for these additional points
  3. The 'Bonus' Program—this is events, screenings or points earned on certain participation drives. These include:
    Cholesterol screening
    Glucose screening
    Preventive measure screenings which include PAP Smears, Mammograms, Prostate checks, Glaucoma screening, Dental checks, Vaccinations
    Approved Sporting Events (i.e. Active.com)
    Approved Instruction Courses
    Challenges (Members' challenges)
    Additional/future health questionnaires through the website
    Benevolent actions such as donating blood, CPR, First Aid, Lifesaving courses
  A more detailed discussion of the Standard Program follows. However, it will be understood that the Bonus Program activities and Client/Supplier Funded Program are supported by this disclosure. The system design must allow for easy additions to the triggers and activities at a later stage.

There are Three Main Points Earning or Interaction Categories:

Points (how do members earn points)—this section has three categories namely Measurement, Effort and Achievement Points.

Going Shopping (how do members look for ways to redeem their currency once their points have been converted)

Redemption (how do members redeem these points once they have decided how to use their currency)

Identifying of Rewards vs. Non-Rewards Members:

This is managed in the registration process and this data must feed this system from a derived source rather than a static field. Requirements, and incorporates the following mechanisms to support the IWP:

Maintenance Screens to set values and frequencies of the rewards process

Event Triggers captured to record reward earning

Viewing of points balances.

Redemption Process

Points Flow

Points Limits and Capping

Individual point's categories have a limit on how many times they can be applied on a time period such as 16 logged exercise sessions per month There is not however a total capping on the number of points that a member can earn Certain points values can increment over time based upon enrolment in the program and these incrementing rewards have a maximum point limit they can increase to such as the Health Snapshot point's allocation.

Bonuses

The system requires the ability to boost points with a bonus. This bonus may be applied on completion of one or a set of activities.

A time limit on completing sets of rewards will apply.

Basic Principles

Point's conversion is fixed at:

1 pt=1 c, hence 100 pts=$1 and 1000 pts=$10.

Flexibility

The system needs to allow for future triggers to be implemented as well as allow for the change of points allocation for activities if the program design is required to change as the company tracks usage and learns about consumer usage.

Further flexibility is required for different requirements from insurance partners, large employers (who for example may wish to increase the value of the Fitness Assessment or award bonuses for certain activities as part of a promotion).

Points Earners

For launch, Points Earners have been defined as individuals aged 18 years or over. In later phases, we may be able to include children earning their own points within the family or parents earning 'Family points' for taking care of their childrens' health.

Category 1—Earning Points

Section 1: Measurement Events

These events are not related to exertion but instead reward good patterns of other health related behavior e.g. undertaking regular screenings and preventative measures, and good patterns of IWP interaction, especially data recording via the Health Zone. Essentially, these are the routine elements and the emphasis is on getting people into good habits. The following is an example allocation system:

A: Registration & Assessment i) IWP Registration and Health Snapshot (Standard)

Trigger=IWP Registration and Health Snapshot completion through the website

Points value=1000 in year 1, 1250 in year 2 and 1500 in year three onwards for continuous membership Frequency=1 per year for points allocation but the member can complete it more frequently if they wish Maximum points allocation per year=1000 in year 1, 1250 in year 2 and 1500 from year 3 onwards if continuous membership Rules=If a member drops out of the IWP and later rejoins, they start again at 1000 points.

ii) Health Zone Measurements (Standard)

Trigger=Taking all 3 biometric HZ measurements (blood pressure, weight and body fat)

Points value=100 per month where all 3 measurements are taken

Frequency=1 per month—this is not set strictly to a calendar month but rather the measurements must be 21 days apart for points to be awarded Maximum Quarterly points allocation=300

Maximum points allocation per year=1200

Rules=Points are only allocated when all 3 measurements are taken each month

Method of data collection=Automatic from the HZ iii) Fitness Assessments (Standard)

Trigger=Member completing a Fitness Assessment

Points value=500

Frequency=2 per annum

Maximum points allocation per year=1000

Rules=1 test each half of the year

Method of data collection=Automatic from assessor interface feeding into database For i), ii), and iii) the combined maximal value per annum is as follows:

Year 1=3200

Year 2=3450

Year 3+=3700

Section 2—Effort Points

A: Regular Exercise i) Self Logged Exercise (Standard)

Trigger=An exercise session logged through the website or Health Zone (HZ)

Points value=10

Frequency=Up to 16 sessions per month

Maximum points allocation per year=2080

Rules=People can log 6 exercise sessions 1 week and 2 the next so the cap only applies to the overall monthly number of sessions Can only log exercises within the last 4 weeks Method of data collection=from within our database via the Health Zone or website Frequency of external data feed=as from within data center database ii) Electronically Logged Exercise (i.e. Monitors, Pedometers) (Standard)

Trigger=Any uploaded exercise session from an electronic device into the database Points value=20

Frequency=Up to 16 sessions per month

Maximum points allocation per year=4160

Rules=Can only upload exercises through the website for a period within the last 4 weeks People can upload 6 exercise sessions 1 week and 2 the next so the cap only applies to the overall monthly number of sessions Method of data collection=Electronic files uploaded from the exercise logging device into the database
Frequency of external data feed=as from within database
B: Quest Participation
Quest Sign Up
Trigger=Signing up to the Quest program
Points value=250
Frequency=As often as the program runs
Maximum points allocation per year=1000
Rules=The members do not gain Quest points for logging exercise as they gain points for logging exercise through the 'self logging' section (i)
Method of data collection=Sign up through the system and hence from the database (HZ or website)
Frequency of external data feed=as from within database
Quest Completion
Trigger=Completion of the Quest Program
Points value=Tiered points for minimum, moderate and maximal participation and completion—this will need to be derived from running an analysis of participation of those people who signed up and categorising them into these three categories i.e. 100 points for minimal, 175 for moderate and 250 for maximal completion
Frequency=As often as the program runs
Maximum points allocation per year=1000
Method of data collection=Analysis of activity data from those members who signed up to the Quest program from within the database
Frequency of external data feed=as from within database
Section 3—Improvement and Achievement Points
A: Health Zone data
i) BMI
Trigger=BMI score in the Ideal range or Improvement in BMI rating
Points value=50
Members earn 50 points if they improve maintain an 'Ideal' score or improve a category i.e. from Obesity 1 to Overweight, or from Overweight to Ideal, from Underweight to Ideal, or Obesity 3 to Obesity 2, or Obesity 2 to Obesity 1.
Frequency=Quarterly—Once per quarter the data is analysed
Maximum points allocation per year=200
Rules=If BMI is over the ideal range and % body fat is within ideal range, then the points allocation will assume that both the BMI and % body fat are within the ideal range i.e. will get the improvement/maintaining points for BMI as well as % body fat.
Method of data collection=HZ data analysis
Frequency of external data feed=as from within data base.
ii) Blood Pressure
Trigger=Ideal score for blood pressure or improvement from less ideal readings to Ideal readings
Points value=50 points for maintaining an 'Ideal' score or, for improving from either Pre-hypertension to Ideal, from Hypertension Stage I to Pre-hypertension or to Ideal, or from Hypertension Stage 2 to Hypertension Stage I or Pre-hypertension or to Ideal.
Frequency=Quarterly—Once per quarter the data is analysed
Maximum points allocation per year=200
Method of data collection=HZ data analysis
Frequency of external data feed=as from within database
iii) Body Fat
Trigger=Acceptable, Good, or Excellent scores for body fat and improvement of body fat results
Points value=50 points for maintaining an Acceptable, Good or Excellent score, OR for improving from Poor to Fair, from Fair to Acceptable and any movement in an upward trend.
Frequency=Quarterly—Once per quarter the data is analyzed
Maximum points allocation per year=200
Method of data collection=HZ data analysis
Frequency of external data feed=as from within database
B: Fitness Assessment Scores
Trigger=Scores of Acceptable, Good or Excellent from the Overall Classification (OC) from the FA or improvement in categories
Points value=500 points for each level of improvement or for maintaining an Acceptable, Good or Excellent OC
Frequency=maximum of twice per year
Maximum points allocation per year=2500 points if a member improves from Poor to Excellent and then maintains this score
Method of data collection=FA data analysis with database
Frequency of external data feed=as within database
Section 4—Bonus Points Section:
A: Intervent Programs (weight Management and Risk Management)
(Client/Supplier Funded)
i) 12 week mentored program:
Trigger=Signing up (first 500 points) and then completion of the 12 week program with 80% attendance to mentoring sessions (further 1000 points)
Points value=500 signing up and 1000 completion with 80% attendance to mentoring sessions
Frequency=can be multiple annually
Maximum points allocation per year=these points are assigned for each Intervent course the member signs up to
Method of data collection=Feed from the Intervent system (finer details will be confirmed as this is worked out)
Frequency of external data feed=as within database.
ii). Self Paced Intervent Program:
Trigger=Signing up (250 points)
Points value=250 points for signing up
Frequency=can be multiple annually
Maximum points allocation per year=these points are assigned for each Intervent course the member signs up to
Method of data collection=Feed from the Intervent system
Frequency of external data feed=as within database.
B: Health Screenings (Client/Supplier Funded or Bonus)
i) Cholesterol
Trigger=Cholesterol value being entered through the HZ software or a data feed from insurer/pharmacy partner/employer
Points value=250 for self reported, another 250 can be earned if the score is validated and within the ideal range
Frequency=points awarded for 1 self entry per year but more entries can be accepted if they are validated readings
Maximum points allocation per year=500
Rules=Points allocated to males and females over 18 years of age
Method of data collection=self reporting through the Health Zone or a data feed from insurer/pharmacy partner/employer
Frequency of external data feed=Monthly
ii) Glucose
Trigger=Glucose value being entered through the HZ software or a data feed from insurer/pharmacy partner/employer
Points value=250 for self reported, 500 for validated entry (passed from approved supply source) that is within the ideal range
Frequency=points awarded for 1 self entry per year but more entries can be accepted if they are validated readings
Maximum points allocation per year=250

Rules=Points allocated to males and females over 18 years of age
Method of data collection=self reporting through the Health Zone or a data feed from insurer/pharmacy partner/employer
Frequency of external data feed=Monthly
iii) Mammogram/Ultrasound
Trigger=Data provided by insurer/employer through a data transfer
Points value=250
Frequency=determined by doctor—open
Maximum points allocation per year=250
Method of data collection=Electronic transfer from insurer/employer
Frequency of external data feed=Monthly
iv) PAP Smear
Trigger=Data provided by insurer/employer through a data transfer
Points value=250
Frequency=determined by doctor—open
Maximum points allocation per year=250
Method of data collection=Electronic transfer from insurer/employer
Frequency of external data feed=Monthly
v) Prostate Check
Trigger=Data provided by insurer/employer through a data transfer
Points value=250
Frequency=determined by doctor—open
Maximum points allocation per year=250
Method of data collection=Electronic transfer from insurer/employer
Frequency of external data feed=Monthly
vi) Glaucoma/Eye Tests
Trigger=Data provided by insurer/employer through a data transfer
Points value=250
Frequency=determined by optometrist—open
Maximum points allocation per year=250
Method of data collection=Electronic transfer from insurer/employer
Frequency of external data feed=Monthly
vii) Dental Checks
Trigger=Data provided by insurer/employer through a data transfer
Points value=250
Frequency=open
Maximum points allocation per year=250
Method of data collection=Electronic transfer from insurer/employer
Frequency of external data feed=Monthly
viii) Vaccinations
Trigger=Data provided by insurer/employer through a data transfer OR by confirmation i.e. via fax by the member as not sure if the insurer or employer would know this info if the member went to a pharmacy or GP
Points value=250
Frequency=open
Maximum points allocation per year=250
Method of data collection=Electronic transfer from insurer/employer OR via confirmation by the member via fax
Frequency of external data feed=Monthly from insurer/employer
C: Approved Sporting/Recreational Events
(Client/Supplier Funded or Bonus)
Trigger=Activity information from activity partner e.g. active.com
Points value=1000
Frequency=4 per year
Maximum points allocation per year=4000
Method of data collection=External data feed
Frequency of external data feed=Weekly
D: Approved Instruction Courses
(Client/Supplier Funded or Bonus)
Trigger=Confirmation a member has completed a course with an approved partner
Points value=100
Frequency=open
Maximum points allocation per year=400
Method of data collection=external data feed from approved partner
Frequency of external data feed=monthly
E: Challenges
(Client/Supplier Funded or Bonus)
i) Quarterly Outbound Challenges:
Trigger=Sign up to the challenge
Points value=100
Frequency=open
Maximum points allocation per year=400
Method of data collection=sign up through website
Frequency of external data feed=as within database.
ii) Members/Corporate Challenges:
Trigger=sign up to the challenge
Points value=100
Frequency=open
Maximum points allocation per year=400
Method of data collection=sign up through website
Frequency of external data feed=
E: Benevolent Actions
(Client/Supplier Funded or Bonus)
i) Donating Blood:
Trigger=member donating blood and confirmation being uploaded to database
Points value=100
Frequency=open
Maximum points allocation per year=800
Method of data collection=external data feed confirming blood donation from e.g. Red Cross USA
Frequency of external data feed=Monthly
ii) First Aid Qualification:
Trigger=confirmation of participation from an approved partner who the member has been trained by
Points value=200
Frequency=1 per annum
Maximum points allocation per year=200
Method of data collection=external data feed from approved partner
Frequency of external data feed=monthly
iii) CPR Qualification:
Trigger=confirmation of participation from an approved partner who the member has been trained by
Points value=200
Frequency=1 per annum
Maximum points allocation per year=200
Method of data collection=external data feed from approved partner
Frequency of external data feed=monthly
iv) Lifesaving Qualification:
Trigger=confirmation of participation from an approved partner who the member has been trained by
Points value=200
Frequency=1 per annum
Maximum points allocation per year=200

Method of data collection=external data feed from approved partner
Frequency of external data feed=monthly
F: Ad-hoc Questionnaires:
(Client/Supplier Funded or Bonus)
Trigger=completion of questionnaire through website
Points value=100
Frequency=open
Maximum points allocation per year=300
Method of data collection=through website and database While certain features and embodiments have been described in detail herein, it will be readily understood that the invention includes all modifications and enhancements within the scope and spirit of the following claims.

What is claimed is:

1. An interactive computer system for managing the health and wellness of an individual, comprising:
   a. an input station configured to enable input of health and wellness information of an individual;
   b. an identifier configured to identify the individual specifically and uniquely when the individual logs on at the input station;
   c. a measuring device configured to measure certain health and wellness information of the individual automatically and automatically input the measured health and wellness information into the input station;
   d. a manual input device configured to enable the individual to input certain other health and wellness information manually;
   e. a server connected to the input station and configured to receive and identify the input health and wellness information as the individual's specific data, the server including a management database configured to store (i) the individual's specific data, (ii) health and wellness data for the population at large, wherein the population at large is any population outside the individuals whose health and wellness are managed by the interactive computer system, and (iii) ideal health and wellness data, the server further including an assessment module configured to track changes in the individual's specific data over time, enable display to the individual of changes in the individual's specific data and display of comparisons of the individual's specific data with health and wellness data for the population at large, and provide feedback information based on the individual's specific data, the feedback information including incentive information configured to encourage the individual to use the interactive computer system regularly and configured to indicate points awarded to the individual for activities by the individual in the individual's specific data; and
   f. a communication network interface coupled to the server and configured to provide to the individual displays of indications of at least two of (i) the individual's specific data, (ii) comparisons of the individual's specific data with health and wellness data for the population at large, (iii) changes in the individual's specific data over time, and (iv) a personalized plan for nutrition and exercise based on the feedback information.

2. The computer system of claim 1, wherein the measuring device includes a scale for weighing the individual and entering the individual's weight.

3. The computer system of claim 1, wherein the measuring device includes a blood pressure monitor for measuring the blood pressure of the individual and entering it into the station.

4. The computer system of claim 1, wherein the manual input device is an alphanumeric keypad.

5. The system of claim 1, wherein the manual input device is a touch screen.

6. The computer system of claim 1, further including Internet connectivity wherein the individual may log on to the server from a device connected to the Internet to obtain the individual's specific data and comparison data.

7. The computer system of claim 1, wherein the manual input device is adapted for setting individual goals selected by the individual.

8. The computer system of claim 7, wherein the computer system is adapted for measuring an individual's progress against the individual goals.

9. The system of claim 8, further including a reward system for providing the individual with incentives for progressing against the individual goals.

10. The computer system of claim 1, wherein respective individual specific data for a group of individuals is maintained as group data by defined group criteria such as age, weight, smoking and drinking habits.

11. The computer system of claim 10, wherein the group data may be accessed by registered users via the Internet.

12. The computer system of claim 1, wherein the server further includes an incentive system configured to assign points for certain activities by the individual and to award the individual with points when the activity is completed.

13. The computer system of claim 12, wherein the points are redeemable for rewards.

14. The computer system of claim 12, wherein the points are sponsored by a third party.

15. An interactive computer system for managing the health and wellness of an individual, comprising:
   a. an input station configured to enable an individual to input specific health and wellness information;
   b. an identifier configured to identify the individual specifically and uniquely when the individual logs on at the input station;
   c. a measuring device configured to measure certain health and wellness information automatically and automatically input the measured health and wellness information into the input station;
   d. a server connected to the input station and configured to receive and identify the health and wellness information as the individual's specific data;
   e. the server including (i) a feedback module configured to assist the individual with measuring health and wellness information, (ii) an assessment module configured to track changes in the individual's specific data over time and enable display of the changes in the individual's specific data and display of comparisons of the individual's specific data with health and wellness data for the population at large, wherein the population at large is any population outside the individuals whose health and wellness are managed by the interactive computer system, and (iii) a rewards module configured to assign incentive points to the individual based on the changes in the individual's specific data; and
   f. a display responsive to the server and configured to provide indications to the individual of the changes in the individual's specific data or the incentive points assigned to the individual.

16. The system of claim 15, wherein the rewards module is further configured to assign points for certain activities by the individual and rewarding the individual with incentive points when the activity is completed.

17. The system of claim 16, wherein the incentive points are redeemable for rewards.

18. The system of claim 16, wherein the incentive points are sponsored by a third party.

* * * * *